US008699026B2

(12) United States Patent
Varghese et al.

(10) Patent No.: US 8,699,026 B2
(45) Date of Patent: Apr. 15, 2014

(54) DETECTOR FOR BIREFRINGENT OBJECTS

(75) Inventors: Babu Varghese, Eindhoven (NL); Rieko Verhagen, Vught (NL); Bart Willem Jan Spikker, Eindhoven (NL); Natallia Eduardauna Uzunbajakava, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 170 days.

(21) Appl. No.: 13/256,513

(22) PCT Filed: Mar. 15, 2010

(86) PCT No.: PCT/IB2010/051100
§ 371 (c)(1),
(2), (4) Date: Sep. 14, 2011

(87) PCT Pub. No.: WO2010/106480
PCT Pub. Date: Sep. 23, 2010

(65) Prior Publication Data
US 2012/0002204 A1  Jan. 5, 2012

(30) Foreign Application Priority Data
Mar. 19, 2009 (EP) .................................. 09155609

(51) Int. Cl.
*G01J 4/00* (2006.01)
(52) U.S. Cl.
USPC .......................................... 356/364; 356/369
(58) Field of Classification Search
USPC ............................ 356/364–369; 600/476, 473
See application file for complete search history.

(56) References Cited

U.S. PATENT DOCUMENTS 3,900,252 A    8/1975   Di Salvo et al.
7,289,210 B2*  10/2007  Jang .............................. 356/364
7,460,248 B2*  12/2008  Kurtz et al. .................... 356/521
2005/0122514 A1  6/2005  Jang
2006/0241495 A1* 10/2006  Kurtz ............................. 600/476
2007/0252997 A1  11/2007  Van Hal et al.
2007/0263226 A1  11/2007  Kurtz et al.
2010/0063491 A1*  3/2010  Verhagen et al. .................. 606/9

FOREIGN PATENT DOCUMENTS

DE    10137340 A1    2/2003
JP       05142156       6/1993
WO   2005102153 A1   11/2005
WO   2006101736 A1    9/2006
WO   2008072151 A2    6/2008
WO   2008120141 A2   10/2008

OTHER PUBLICATIONS

Roger K. Curtis et al: "Birefringence: Polarization Microscopy as a Quantitative Technique of Human Hair Analysis", J. Soc. Cosmet. Chem. vol. 27, No. 9, pp. 411-431, Sep. 1976, XP002587881.

* cited by examiner

*Primary Examiner* — Tara S Pajoohi Gomez

(57) ABSTRACT

A detector for detecting a birefringent object near a skin surface of a human body part or an animal body part includes a source for emitting optical radiation having first and second wavelengths and an incident polarization state. An imaging unit is configured to image the birefringent object near the surface includes a detection unit for detecting optical radiation scattered and/or reflected by the birefringent object and/or the surface at the first and second wavelengths. A control unit is configured to process a signal from the detection unit for discrimination between the birefringent object and the surface. The detection unit is configured to detect scattered and/or reflected optical radiation coming from the birefringent object and/or the surface, having a first polarization state corresponding to the incident polarization state and a second polarization state being different from the first polarization state.

17 Claims, 5 Drawing Sheets

DETECTOR FOR BIREFRINGENT OBJECTS

FIELD OF THE INVENTION

The invention relates to the field of detectors and to the field of methods adapted for detecting a birefringent object near a surface, such as a hair near a skin surface. The invention also relates to the field of shaving devices, preferably adapted for detecting and for cutting a hair near a skin surface of a human body part or an animal body part, wherein the detector is preferably adapted for being integrated in the shaving device.

BACKGROUND OF THE INVENTION

Document WO 2008/072151 A2 describes a device for imaging a skin object near a skin surface of a body part, comprising a light source and a detector for detecting radiation returning from the object, wherein the device further comprises a linear, elliptical, or preferably circular polarizer between the source and the skin surface. The device also comprises a ratio increaser means for increasing the ratio of radiation coming from the object to radiation coming from the skin surface. The ratio increaser may be an additional or the same elliptical polarizer. Using elliptically or even circularly polarized light makes hair detection independent of the orientation of hair with respect to light direction and polarization, which renders the detection more reliable. The document further describes an imaging method and a hair-shortening device and method.

An entry point in optical shaving technology with a potential to improve closeness of the shaving process comprises the development of an optical shaver, also referred to as shaving device in the following, wherein the shaving device is adapted for cutting a hair at the skin surface or below the skin surface of a human or animal body part or any other body part.

However, it is difficult to detect and localize each hair with a high resolution and ensure that the shaving process is performed only at the desired location, i.e. at the position of a hair and not at the position of the human or animal skin near a human or animal body part, respectively. At the same time, the shaving process must be reliable. Furthermore, the costs for implementing such a shaving process are high and such a shaving device is complex.

SUMMARY OF THE INVENTION

It is an object of the invention to provide a possibility to improve closeness in the shaving process and thus to achieve a high resolution, a high efficacy and a high reliability, and preferably, at the same time, a high shaving safety, a low energy consumption in conjunction with a simple device setup that contributes to reducing the implementation costs.

This object is achieved by the subject matter of the independent claims. Preferred embodiments are defined in the sub-claims.

According to a first aspect of the invention, this object is achieved by a detector, adapted for detecting a birefringent object near a surface, comprising a source adapted for emitting optical radiation comprising at least a first wavelength, a second wavelength and an incident polarization state, and an imaging unit adapted for imaging the birefringent object near the surface, wherein the imaging unit comprises a detection unit adapted for detecting optical radiation scattered and/or reflected by the birefringent object and/or the surface at the first wavelength and at the second wavelength, and a control unit adapted for processing a signal from the detection unit for discrimination between the birefringent object and the surface, and wherein the detection unit is arranged for detecting scattered and/or reflected optical radiation coming from the birefringent object and/or the surface, comprising a first polarization state corresponding to the incident polarization state and a second polarization state being different from the first polarization state.

The term "near a surface" means "on and/or below the surface". The surface preferably corresponds to a skin surface of a human body part or an animal body part, and the birefringent object preferably corresponds to hair. In the following, the detector is also referred to as hair detector, preferably adapted for being integrated in a shaving device. It goes without saying that the term "a hair near a skin surface" means that the hair protrudes from the skin surface and/or is located on or somewhat below the skin surface. The control unit preferably processes a first signal measured at the first wavelength relative to a second signal measured at the second wavelength for discrimination between the birefringent object and the surface. The optical radiation emitted from the source preferably comprises a wavelength $\geq 180$ nm and/or $\leq 3000$ nm, more preferably a wavelength $\geq 200$ nm and/or $\leq 2000$ nm.

Preferably, the detection unit of the imaging unit is positioned in an optical path of the optical radiation between the source and the birefringent object.

Preferably, the second polarization state is orthogonal or perpendicular to the first polarization state. However, it is also possible that the first polarization state and the second polarization state are not orthogonal to each other, showing a slight deviation, but still both polarization states remain separable from each other.

According to the invention, differential polarization imaging is applied in order to improve discrimination and, thus, detection of a birefringent object near a surface. If used in a shaving device, shaving quality can be enhanced. Strictly speaking, the detection unit is preferably adapted for detecting optical radiation comprising a horizontal and a vertical polarization at each wavelength. This kind of detection corresponds to a polarization-sensitive confocal detection of optical radiation scattered and/or reflected by a hair. Therefore, it becomes possible to detect or discriminate a polarization change induced by the birefringence of the hair or any other birefringent object that needs to be detected.

According to a preferred embodiment of the invention, the first wavelength and the second wavelength are related to two predetermined single wavelengths being different from each other, or are comprised by at least two predetermined wavelength ranges being at least partially different from each other. In general, the incident polarization state can be radiated directly to the birefringent object near the surface. However, the imaging unit preferably further comprises a polarization transformer adapted for transforming the incident polarization state comprised by the optical radiation emitted from the source to another polarization state comprised by an output beam directed to the surface.

It is an important idea of the invention to make hair detection possible in almost any case, since preferably each hair is detected and thus the detection of false-negatives is greatly reduced. The detection of false-positives is further greatly reduced due to discrimination between a hair and a surrounding medium, such as air or skin.

According to another preferred embodiment of the invention, the imaging unit further comprises a plurality of lenses and/or a focusing unit adapted for focusing the output beam directed to the surface. Therefore, only the desired location on the skin surface is illuminated by the output beam. The focusing unit preferably comprises a lens, a microscopic objective and/or an optical element, such as an optical blade. A pinhole is preferably arranged in the optical path between the polarization transformer and the focusing unit. Preferably, the incident polarization state comprises a linear polarization state, a circular polarization state and/or an elliptical polarization state, and the transformation to another polarization state comprises a polarization state corresponding to a polarization state different from the incident polarization state. The polarization transformer preferably comprises a quarter wave plate or any other retardation wave plate that can be adequately applied.

A polarization transformer comprises an optical retardation plate which has its usual meaning herein, i.e. a plate which is transparent to the used optical radiation and which has the property that the speed of propagation for a polarization direction in a first orientation, also referred to as "fast axis", is higher than in the direction perpendicular thereto, also referred to as "slow axis". This causes a phase difference between the two component parts of a light wave along those two directions. If the appropriate angle with respect to the direction of polarization of the linearly polarized light and the thickness of the retardation plate, which determines the phase difference, are suitably selected, the net result will be that the light becomes elliptically polarized. It is also possible to make circularly polarized light in a manner known to those skilled in the art.

According to yet another preferred embodiment of the invention, the imaging unit further comprises a ratio increaser unit arranged in an optical path of the optical radiation between the surface or the birefringent object and the detection unit, wherein the ratio increaser unit is adapted for increasing the ratio of the optical radiation that returns from the birefringent object to the optical radiation that returns from the surface. Preferably, the ratio increaser unit comprises at least one of a beam splitter and a polarization beam splitter, more preferably a beam splitter and a polarization beam splitter arranged in a common optical path, and/or a Faraday isolator.

According to yet another preferred embodiment of the invention, the source comprises at least one of a semiconductor laser, such as a laser diode, a solid state laser, such as a fiber laser, and a broadband source, such as a super luminescent laser diode, adapted for emitting incoherent optical radiation. It is noted that not only sources emitting coherent optical radiation are applicable but also incoherent sources can advantageously be used. The source can be any source working in pulsed or continuous-wave mode.

Preferably, the source comprises a broadband source, such as a super luminescent laser diode, preferably with a bandwidth of at least 30 nm, more preferably a bandwidth of at least 50 nm, and most preferably a bandwidth of at least 80 nm. The predetermined wavelength range is preferably chosen in function of at least one of the following parameters: diameter of the birefringent object, birefringence of the birefringent object and center wavelength of the source. Preferably, the center wavelength of the broadband source comprises the range between 400 nm and 2000 nm, more preferably the range between 800 nm and 1100 nm, most preferably the range between 1400 nm and 700 nm. According to yet another preferred embodiment of the invention, the center wavelength of the broadband source comprises the range between 810 nm to 850 nm.

According to yet another preferred embodiment of the invention, the source comprises a first circularly polarized optical radiation source and a second circularly polarized optical radiation source, wherein a combiner, preferably a dichroic beam combiner, combines a first beam emitted from the first circularly polarized optical radiation source and a second beam emitted from the second circularly polarized optical radiation source. Preferably, the control unit is adapted for performing a mathematical operation, more preferably a subtraction and/or a division, on a first signal measured at the first wavelength or at a first predetermined wavelength range relative to a second signal measured at the second wavelength or at a second predetermined wavelength range for discrimination between the birefringent object and the surface. Preferably, the detection unit comprises at least two photo detectors, more preferably at least four photo detectors. Most preferably each photo detector corresponds to an avalanche photo detector, wherein the optical path between each photo detector and the ratio increaser unit comprises at least a focusing element or a combiner, wherein the combiner preferably corresponds to a dichroic beam splitter.

According to a second aspect of the invention, the above mentioned object is achieved by a shaving device, adapted for detecting and cutting a hair near a skin surface of a human body part or an animal body part, comprising a detector according to the first aspect of the invention and adapted for detecting the hair, wherein the shaving device further comprises an optical cutting source, preferably a cutting laser, and wherein the control unit of the detector is adapted for controlling the optical cutting source which is arranged to supply an amount of optical energy to at least a portion of at least one hair and is adapted for cutting the hair.

According to a preferred embodiment of the invention, the shaving device further comprises a glass plate adapted for providing a plain surface to the skin surface comprising at least one hair and/or an element adapted for manipulating hairs protruding from the skin. Further, a refractive index matching medium adapted for providing a refractive index corresponding to a refractive index of the skin surface of a human or an animal body part is preferably comprised by the shaving device.

According to a third aspect of the invention, this object is achieved by a method, adapted for detecting a birefringent object near a surface, comprising the steps of: a) emitting optical radiation comprising at least a first wavelength, a second wavelength and an incident polarization state, b) imaging the birefringent object near the surface, wherein imaging comprises detecting scattered and/or reflected optical radiation coming from the birefringent object and/or the surface at the first wavelength and at the second wavelength, and comprising a first polarization state corresponding to the incident polarization state and a second polarization state being different from the first polarization state, and c) processing a signal for discrimination between the birefringent object and the surface. It goes without saying that the method steps are performed for at least the first wavelength and the second wavelength. According to a preferred embodiment of the invention, the method steps are performed for at least two predetermined wavelength ranges.

It is noted that the polarization change induced by the hair is wavelength dependent and this is due to hair birefringence. When using at least two wavelengths, for instance, a first wavelength and a second wavelength for illumination, and once these wavelengths are detected separately, the differences in polarization change in different wavelength channels are recognizable. It is noted that the latter statement is not valid for the skin since upper layers of the skin are not birefringent. Therefore, in at least two wavelength channels, the hair appears to be different due to the changes in polarization, whereas the skin remains the same or almost unmodified. This leads to a large hair-skin specificity.

According to a preferred embodiment of the invention, instead of using at least two discrete wavelengths, a broadband light source is used. The whole spectrum of the broadband source is preferably divided into a set of at least two wavelength ranges. Using a broadband source emitting in the range between 600 nm and 900 nm, for instance, three predetermined wavelength ranges are chosen, such as the range between 600 nm and 700 nm representing the first predetermined wavelength range, the range between 700 nm and 800 nm representing the second predetermined wavelength range, and the range between 800 nm and 900 nm representing the third predetermined wavelength range. According to another preferred embodiment of the invention, the wavelength range provided by the broadband source is divided into two wavelength channels, such as in the range between 600 nm to 750 nm representing the first predetermined wavelength range, and in the range between 750 nm and 900 nm representing the second predetermined wavelength range. Accordingly, dependent on how many channels are chosen for the application, the wavelength range provided is split into at least two wavelength channels. Using different wavelengths, different polarization changes in hair, but not in skin, are preferably induced.

It is worth noting that the invention applies the principle of polarization-sensitive confocal laser scanning microscopy, PSCLSM for short, adapted for improving hair detection efficiency. Therefore, detection and localization of a birefringent object, such as a hair, showing a high shaving efficacy and specificity becomes possible. It is noted that each hair is detectable and thus false-negatives are avoided. Advantageously, this is performed with a high resolution, more preferably with micron-resolution. At the same time the maximum hair-skin-contrast is achieved and thus false-positives are avoided, which also corresponds to the reduction of skin irritation and to an increase in shaving safety. Laser-induced optical breakdown, LIOB for short, adapted for cutting a hair is advantageously only created at the desired location of the hair near a skin surface. Alternatively, a hair can be cut based on thermal absorption. It is worth noting that also a low energy consumption of the optical cutting source comprised by the shaving device is achieved since the optical cutting source does not need to be continuously on and, therefore, energy can be saved.

It is an important idea of the invention to apply the principle of confocal laser scanning microscopy, CLSM for short. It is worth noting that improved closeness is obtained since a hair is detected as close as possible to the skin surface of a human or animal body part, such as a leg, an arm or a face.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
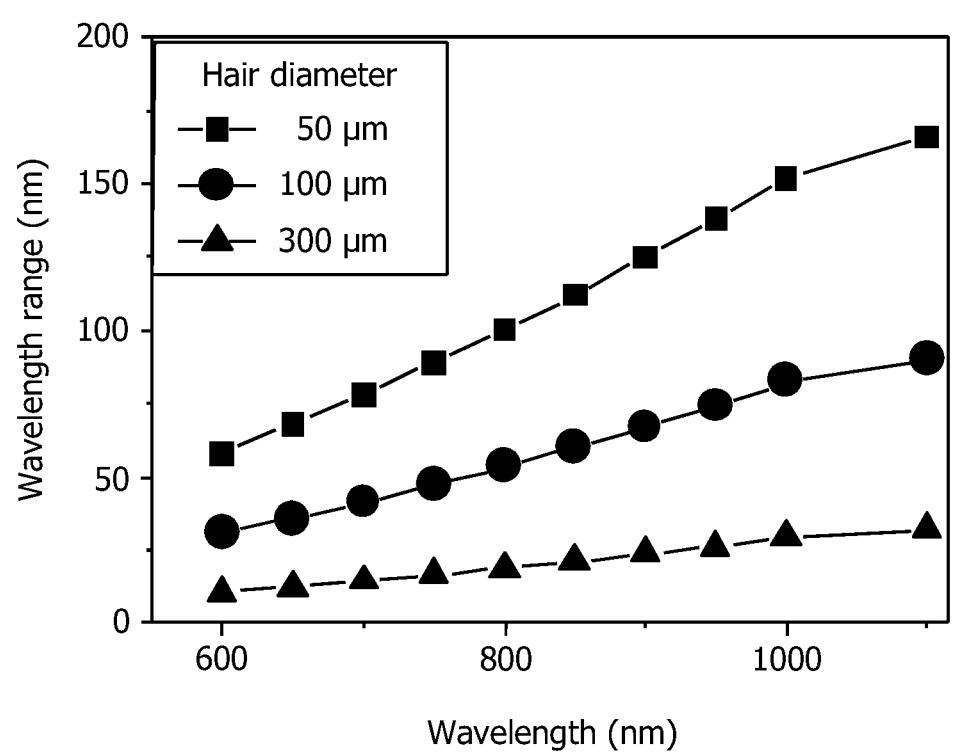
FIG. 1 shows a plot of a wavelength range between two sources as a function of wavelength for different hair diameters according to a first preferred embodiment of the invention.

In CLSM-based hair detection, discrimination between a hair and skin surface is difficult due to skin reflectance. Polarization-sensitive confocal detection of light scattered and/or reflected by a hair adapted for increasing the specificity and efficacy of detection is going to be described hereinafter by means of four preferred embodiments of the invention. The principle is based on discriminating the polarization change induced by the birefringence of a hair, preferably the birefringence of the hair cortex, from the background skin signal. In CLSM, a hair appears either as a bright or a dark object, depending on the direction of the incident polarization state or the electric field with respect to the hair axis.

At the same time, the signal from the skin remains independent of the direction of the incident polarization state. This is due to superficial layers of the skin surface which are not birefringent. Hence, a polarization change provides the basis for discrimination between a hair and the skin surface. The change in polarization of a birefringent object, such as a hair, is chosen as a function of at least one of the following parameters: wavelength, such as center wavelength of the source, hair birefringence and hair diameter. Differential polarization imaging is applied, i.e. light or radiation comprising a first polarization state corresponding to an incident polarization state and, in a second polarization state, being perpendicular, also referred to as orthogonal, to the first polarization state is detected. This is preferably done by illuminating either with at least two circularly polarized light sources of nearly the same wavelengths or with a broadband source adapted for emitting incoherent radiation. According to other preferred embodiments of the invention, also other sources are applicable.

It is ensured that the shaving process is created only at a desired location. The discrimination between a hair and the surrounding medium, such as skin surface, air, foam, water or an index matching fluid, is performed in order to avoid false-positives and thus to reduce skin irritation. Discrimination between a hair and skin surface preferably comprises two criteria: a high signal and the hair shape. The hair shape is important since a high signal per se is difficult to be used as a specific feature in order to discriminate between a hair and skin surface. This is due to dry skin, sebum and/or bubbles due to immersion fluid which can result in a high signal observed in the measurement. The immersion fluid is applied to the hair for cutting using LIOB. However, the use of immersion fluid adapted for thermal cutting of a hair is also possible.

In CLSM, a sample, such as a hair, is illuminated using a light beam or radiation, such as optical radiation, preferably comprising a linear polarization state and detecting radiation preferably comprising a polarization state being orthogonal to the polarization state of the illuminating beam. A birefringent object, such as a hair, appears as a sample exhibiting a different brightness depending on the direction of the incident polarization state with respect to the axis of the birefringent object. However, the signal originating from the skin does not show such a dependency due to the fact that superficial layers of the skin are not birefringent. Hence, the amount of light or radiation originating from the skin comprising a polarization state being orthogonal to the incident polarization state does not depend on the orientation of the incident polarization. Therefore, a signal adapted for recognizing a hair can simply be obtained by subtracting preferably two images acquired using different polarization states of the illuminating light or radiation. A control unit subtracts and/or divides a signal comprising a first polarization state from a signal that comprises a second polarization state, wherein the second polarization state is preferably orthogonal to the first polarization state.

According to a first preferred embodiment of the invention, the values for the ordinary and extraordinary refractive indices for hair, i.e. $n_O$ and $n_E$, correspond to 1.541 and 1.548, respectively. The corresponding value of birefringence $\Gamma$, i.e. corresponding to the difference between extraordinary and ordinary refractive indices, is equal to 0.007. For a given hair diameter and birefringence, the wavelengths for the expected phase radiation of it between two polarizations, dedicated to the fast and slow axis of the birefringent object, can be calculated by applying the following formula:

Retardation=$2\pi(n_O-n_E)\cdot$path length in the hair$/\lambda$.

The maximum signal originating from the hair is expected for a phase retardation of $\pi$. FIG. 1 shows a plot of wavelength ranges required between two sources for different hair diameters as a function of wavelength in order to achieve a phase retardation of $\pi/4$. It can be seen from FIG. 1 that the smaller the hair diameter, the longer the wavelength range needed. Further, it can be seen that with increasing wavelength the wavelength range needed increases almost linearly.

Figure 2:
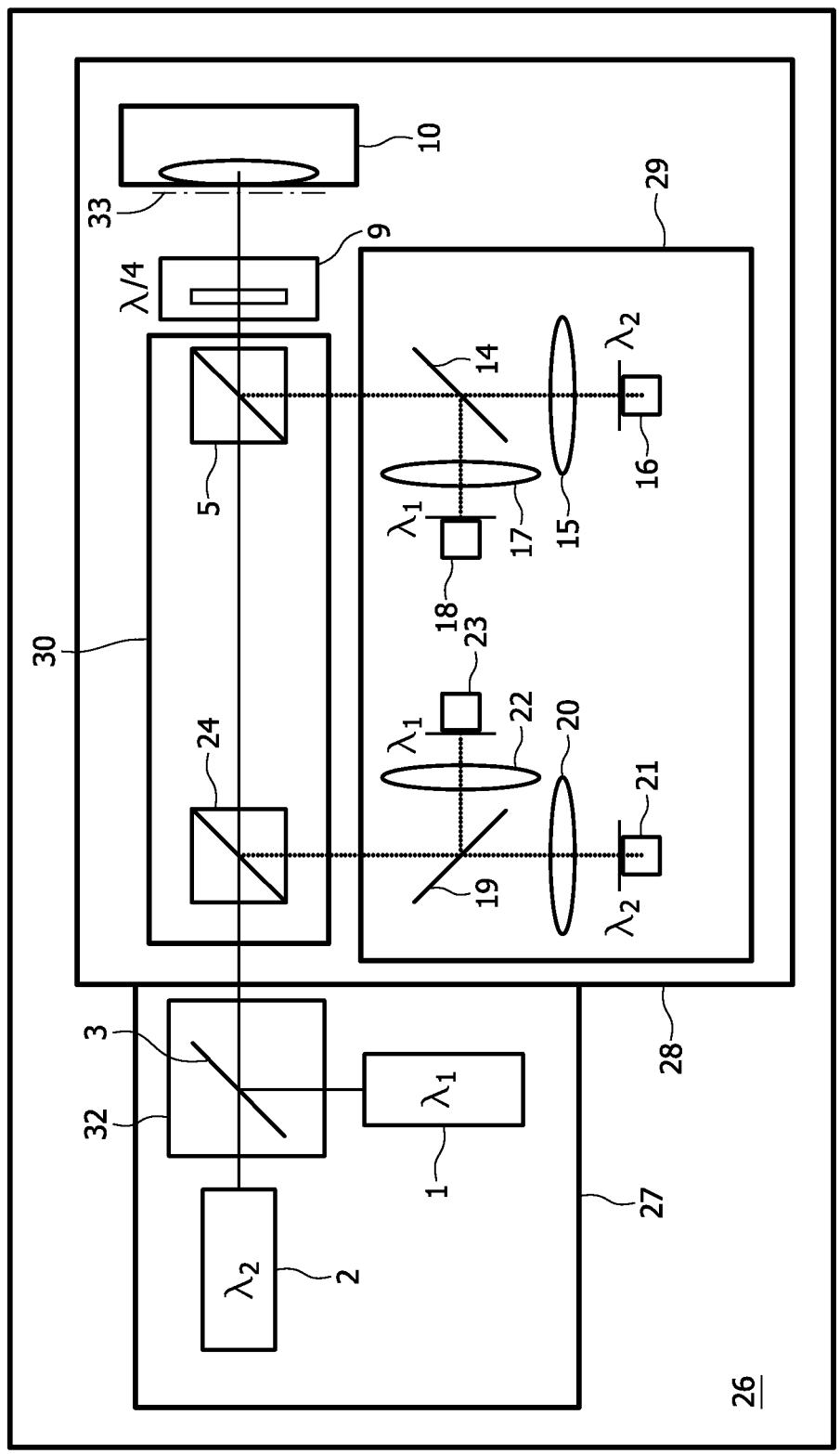
FIG. 2 shows a hair detector according to a second preferred embodiment of the invention.

A hair detector 26 according to a second preferred embodiment of the invention is shown in FIG. 2. The hair detector 26 is based on a source 27 comprising two light sources 1, 2 of nearly the same wavelengths and circular polarization states following on the sample, i.e. a hair. The source 27 is adapted for emitting optical radiation comprising an incident polarization state. According to the second preferred embodiment of the invention, the source 27 comprises a first circularly polarized optical radiation source 1 and a second circularly polarized optical radiation source 2, wherein a combiner 32, according to the second preferred embodiment of the invention a dichroic beam combiner 3, combines a first beam emitted from the first circularly polarized optical radiation source 1 and a second beam emitted from the second circularly polarized optical radiation source.

The hair detector 26 further comprises an imaging unit 28 adapted for imaging a hair on a skin surface of a human or animal body part, wherein the imaging unit 28 comprises a detection unit 29 adapted for detecting optical radiation scattered and/or reflected by the hair and a control unit adapted for processing a signal from the detection unit 29 in order to recognize the hair. It is noted that the control unit is not shown in FIG. 2. According to the second preferred embodiment of the invention, the detection unit comprises four avalanche photo detectors 16, 18, 21, 23, wherein the optical path between each photo detector and a ratio increaser unit 30 comprises at least a focusing element 15, 17, 20, 22 or a combiner 14, 19, wherein the combiner 14, 19 corresponds to a dichroic beam splitter according to the second preferred embodiment of the invention.

Furthermore, the imaging unit 28 further comprises a polarization transformer 9. According to the second preferred embodiment of the invention, the polarization transformer 9 corresponds to a quarter wave plate, adapted for transforming the incident polarization state comprised by the optical radiation emitted from the source 27 to another polarization state comprised by an output beam directed to the skin surface. The detection unit 29 is positioned or arranged in an optical path of the optical radiation between the source 27 and the skin surface and/or the hair and is adapted for detecting scattered and/or reflected optical radiation comprising a first polarization state corresponding to the incident polarization state and a second polarization state being orthogonal to the first polarization state. According to the second preferred embodiment of the invention, the imaging unit 28 further comprises a lens comprised by the focusing unit 10, wherein the lens is adapted for focusing the output beam directed to the skin surface. Moreover, a pinhole 33 is arranged in the optical path between the polarization transformer 9 and the focusing unit 10. According to the second preferred embodiment of the invention, the ratio increaser unit 30 arranged in an optical path of the optical radiation between the skin surface and the detection unit 29 is adapted for increasing the ratio of the optical radiation that returns from the hair to the optical radiation that returns from the skin surface, wherein the ratio increaser unit 30 comprises a beam splitter 24 being nearly or completely insensitive to a polarization change and a polarization beam splitter 5 being polarization-sensitive.

Linearly polarized light emitted from the two light sources 1, 2 is combined by a combiner 32 and is transmitted through a beam splitter 24 and a polarization beam splitter 5, PBS for short. When linearly polarized light traverses through a polarization transformer 9 in such a way that the electric field vector is oriented at 45 degrees with respect to the fast axis of the polarization transformer, the resulting polarization state comprises a circular polarization state. The circularly polarized light comprised by the resulting light beam can be represented as a sum of two orthogonal linearly polarized components shifted in phase by plus or minus 90 degrees. This light beam is then focused by a focusing element 10 at the skin surface comprising a hair. Light is partially reflected at the interface between the skin and the immersion medium, such as air, water or any other medium, and at the interface between a hair and a medium and also scattered by the hair and the skin.

The birefringence of the hair cortex induces a polarization change which is chosen as a function of hair diameter and wavelength. Light reflection from the medium-skin interface comprises a reflection from a dielectric surface comprising a refractive index larger than the refractive index of the light propagation medium, such as air for which it holds that n~1. This introduces a phase shift of 180 degrees of one of the components of circularly polarized light. Once the reflected and/or scattered light from both hair and skin propagates back to the polarization transformer 9, the resulting polarization state comprises a linear polarization state comprising the same or a different orientation than that of the incident polarization state of the incident light, depending on the polarization change. The light or radiation comprising a polarization state being orthogonal to the incident polarization state is reflected by the PBS 5 and the parallel polarization state is transmitted to the beam splitter 24. In both channels, each wavelength is detected separately, comprising a polarization state that is the same as and perpendicular to that of the incident polarization state.

Figure 3:
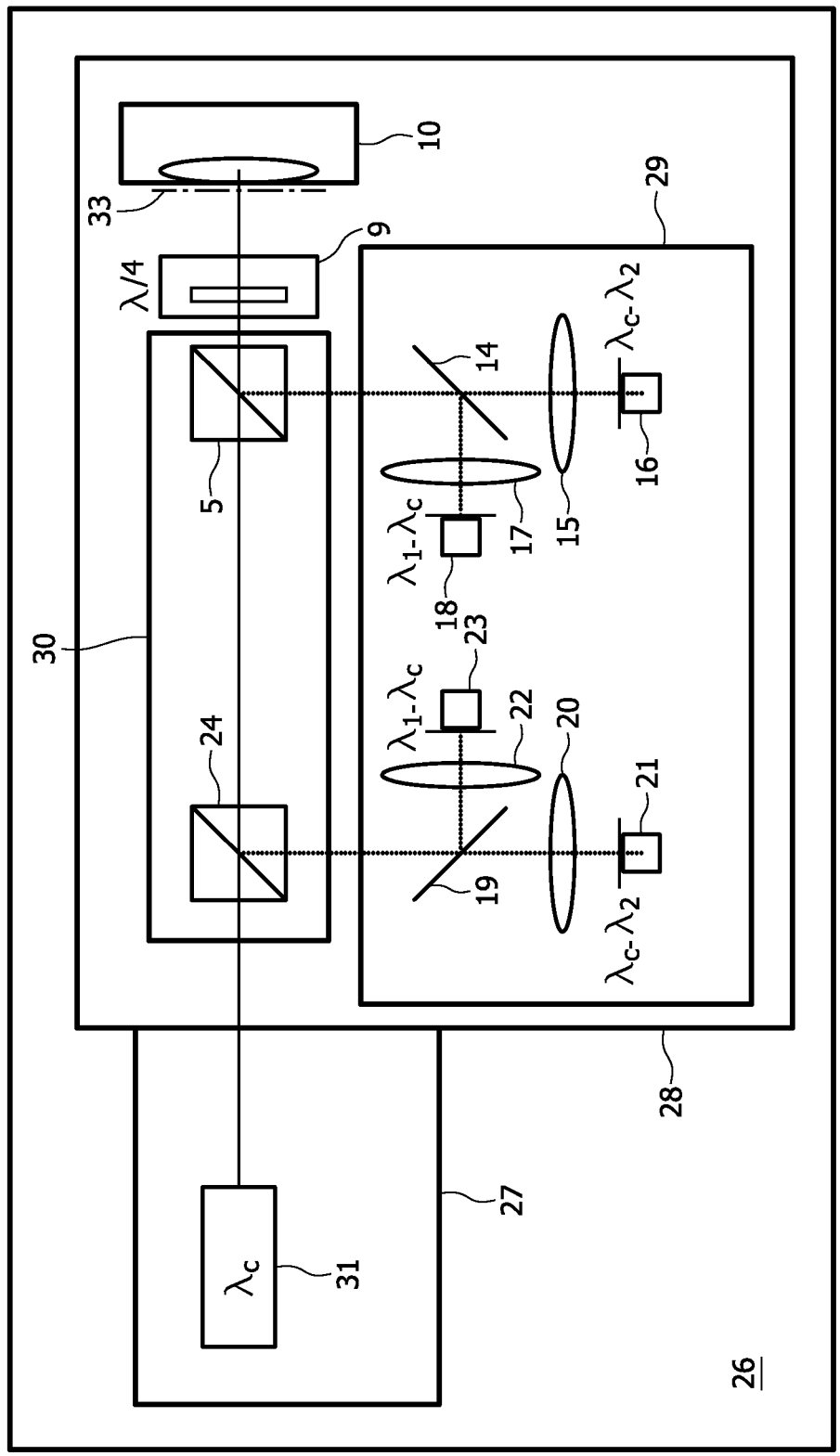
FIG. 3 shows a hair detector according to a third preferred embodiment of the invention.

According to a third preferred embodiment of the invention, the source 27 corresponds to a broadband source 31, which is shown in FIG. 3. The broadband source corresponds to a super luminescent laser diode emitting in the ultraviolet-near infrared spectral range, UV-NIR for short, comprising a bandwidth of at least 50 nm and a central wavelength of 830 nm. Differential polarization imaging is applied for light detected comprising two polarization states, i.e. a polarization state being equal to the incident polarization state or being shifted by 180 degrees and a polarization state being perpendicular to the incident polarization state used for at least two wavelength ranges, such as from a first wavelength to the center wavelength and from the center wavelength to a second wavelength. This offers even more advantages if a broadband source 31 is applied instead of two light sources, such as the light source according to the second preferred embodiment of the invention. Since the polarization change for two specific wavelengths is chosen as a function of hair diameter, which in turn varies between 50 µm and 300 µm, the use of a super luminescent laser diode, SLD for short, makes the performance of the system independent of the hair diameter. The detection unit 29 detects scattered and/or reflected optical radiation in such predetermined wavelength ranges.

Figure 4:
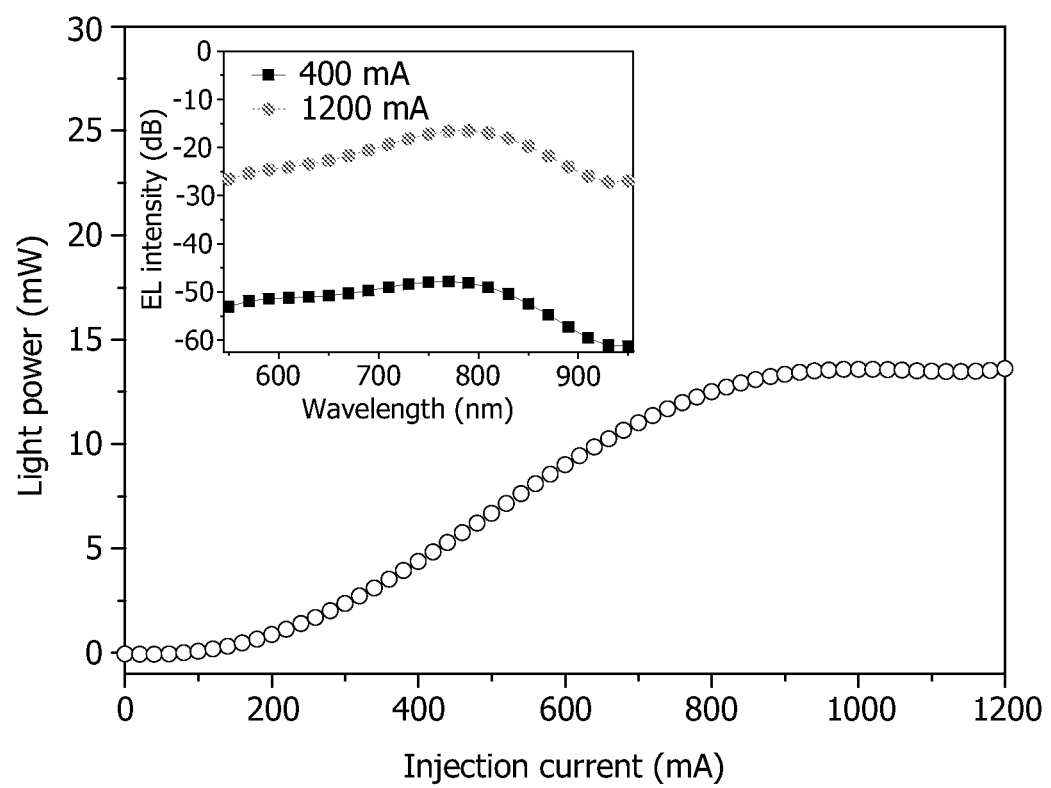
FIG. 4 shows a light power vs. injection current characteristic of a super luminescent diode according to the third preferred embodiment of the invention.

The spectral bandwidth of the SLD is tuned by changing the drive current and temperature. This makes it possible to optimize the performance of the system, depending on the requirements needed. At low drive currents, a laser diode shows multimode operation and, therefore, a number of axial modes are excited within the Gaussian gain profile, resulting in an effective larger spectral bandwidth. As the drive current is increased, a particular mode is preferentially excited and the spectral bandwidth is reduced. A light or optical power spectrum as a function of drive current representing the spectral bandwidth variation and the optical power vs. injection current characteristics of the SLD is shown in FIG. 4, according to the third preferred embodiment of the invention. The inset shows the electroluminescence intensity spectra, EL intensity spectra for short, of the SLD for different currents. As expected, the light power increases with increasing current, however only to a saturation value. From a perspective of system implementation, this reduces the costs and size of the device.

Figure 5:
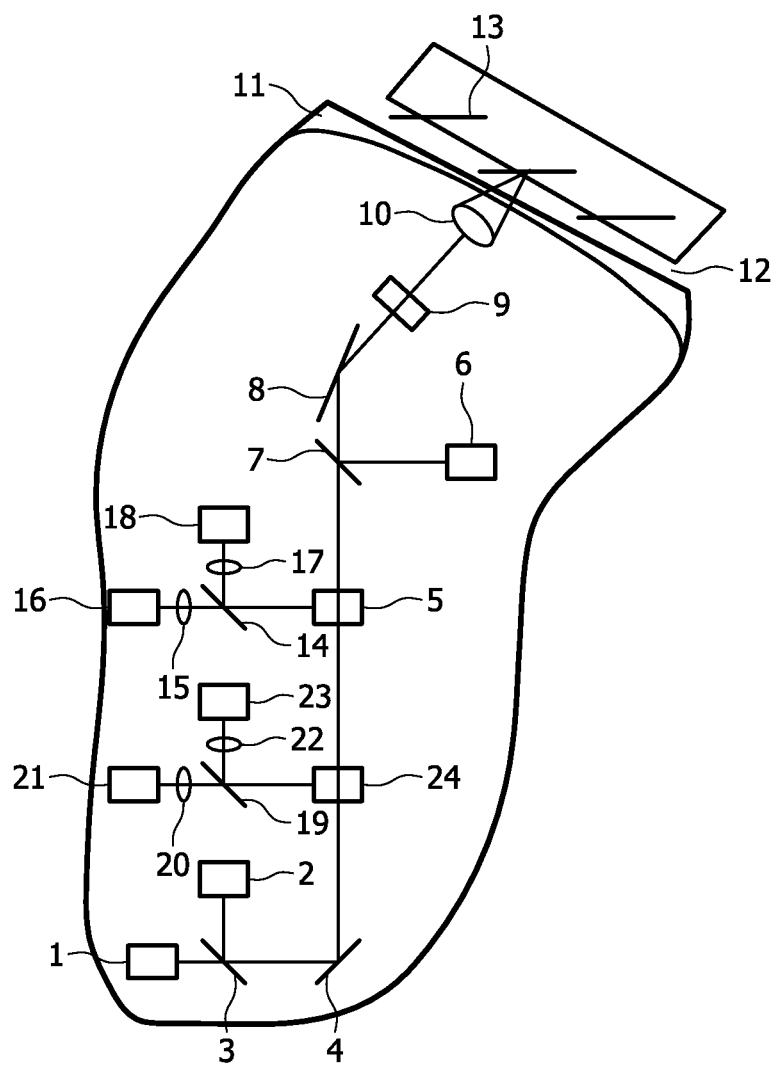
FIG. 5 diagrammatically shows a shaving device according to a fourth preferred embodiment of the invention.

FIG. 5 shows a fourth preferred embodiment of the invention, diagrammatically illustrating a shaving device 25. Herein, as in all of the drawings, similar parts are denoted by the same reference numerals. The shaving device 25 is adapted for detecting and for cutting a hair. The shaving device 25 comprises the hair detector 26 according to the second preferred embodiment of the invention, and is adapted for detecting the hair. The shaving device 25 further comprises a cutting laser comprised by an optical cutting source 6 arranged to supply an amount of optical energy to at least a portion of at least one hair and adapted for cutting the hair. Furthermore, the shaving device 25 comprises a glass plate 11 adapted for providing a plain surface, and a refractive index matching medium 12 adapted for providing a refractive index corresponding to a refractive index of a skin surface 13 of a human or animal body part. Moreover, FIG. 5 also shows a reflecting mirror 4 for the detection wavelengths comprised by the dichroic beam combiner 3, a further reflecting mirror 7 at an end of the hair detector 26, wherein the reflecting mirror 7 is adapted for separating the radiation emitted from the hair detector 26 and the optical cutting source 6, and a scanning mirror 8.

An application of the invention is imaging birefringent objects, such as a hair, in a non-birefringent background, such as near skin. By applying the principle described, a high contrast is obtainable. Therefore, it becomes possible to detect hair with micron resolution and increased hair-skin contrast. Furthermore, it becomes possible to cut the hair with methods, such as LIOB methods or thermal methods. The increased specificity of the measurements, i.e. reducing false-positives, makes discrimination between a hair and a skin structure distinct. This improves the detection efficiency and thus significantly improves the shaving quality.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An apparatus for detecting a birefringent object near a skin surface, comprising:
  a source configured to emit first optical radiation over an optical path to the birefringent object, the first optical radiation comprising at least a first wavelength, a second wavelength and an incident polarization state;
  a detector configured to detect second optical radiation having orthogonal first and second polarization states, the first polarization state corresponding to the incident polarization state, the second optical radiation is the first optical radiation scattered and/or reflected by the birefringent object and the skin surface received over the optical path; and
  a processor configured to distinguish between the birefringent object and the skin surface using the first polarization state and the second polarization state of the second optical radiation.

2. The apparatus according to claim 1, wherein the first wavelength and the second wavelength are related to two different predetermined single wavelengths, or are comprised by at least two at least partially different predetermined wavelength ranges.

3. The apparatus according to claim 1, further at least partially different a polarization transformer configured to transform the incident polarization state to another polarization state before the first optical radiation reaches the skin surface.

4. The apparatus according to claim 3, further comprising a focusing unit configured to focus first optical radiation to the skin surface.

5. The apparatus according to claim 4, wherein the focusing unit comprises one or more of a lens, a microscopic objective and an optical blade.

6. The apparatus according to claim 4, further comprising a ratio increaser arranged in the optical path and configured to increase a ratio of the second optical radiation that returns from the birefringent object to the second optical radiation that returns from the skin surface.

7. The apparatus according to claim 4, further comprising a pinhole arranged in the optical path between the polarization transformer and the focusing unit.

8. The apparatus according to claim 6, wherein the ratio increaser comprises at least one of a beam splitter insensitive to a polarization change, a polarization sensitive beam splitter, and a Faraday isolator.

9. The apparatus according to claim 6, wherein the source comprises a broadband source having a super luminescent laser diode with a bandwidth selected from at least 30 nm, at least 50 nm, and at least 80 nm.

10. The apparatus according to claim 6, wherein the first wavelength and the second wavelength are in at least two different predetermined wavelength ranges, and wherein at least one of the at least two different predetermined wavelength ranges is chosen as function of at least one of a diameter of the birefringent object, birefringence of the birefringent object, and a center wavelength of the source.

11. The apparatus according to claim 3, wherein the incident polarization state comprises a linear polarization state, a circular polarization state and/or an elliptical polarization state, and the another polarization state comprises a polarization state corresponding to a polarization state different from the incident polarization state.

12. The apparatus according to claim 1, wherein the source comprises:
   a first circularly polarized optical radiation source configured to emit a first beam; and
   a second circularly polarized optical radiation source configured to emit a second beam; and
   a combiner configured to combine the first and second beams.

13. The apparatus according to claim 1, wherein the processor is further configured to process a mathematical operation selected from at least one of a subtraction and a division on a first signal measured at the first wavelength or at a first predetermined wavelength range relative to a second signal measured at the second wavelength or at a second predetermined wavelength range for discrimination between the birefringent object and the skin surface.

14. The apparatus according to claim 1, further comprising a plurality of photo detectors selected from at least two photo detectors, and at least four photo detectors, each photo detector
   corresponding to an avalanche photo detector,
   having a second optical path to the ratio increaser; and
   comprising at least one of a focusing element and a combiner including a dichroic beam splitter.

15. A shaving device for detecting and cutting a birefringent object including hair near a skin surface of a human body part or animal body part, the shaving device comprising:
   a source for emitting first optical radiation over an optical path to the birefringent object, the first optical radiation comprising at least first and second wavelengths and an incident polarization state;
   a detector configured to detect second optical radiation having orthogonal first and second polarization states, the first polarization state corresponding to the incident polarization state, the second optical radiation is the first optical radiation scattered and/or reflected by the birefringent object and the skin surface received over the optical path;
   an optical cutting source configured to cut the hair; and
   a processor configures to:
      distinguish between the birefringent object and the skin surface using the second optical radiation, and
      supply optical energy to at least a portion of the hair for cutting the hair.

16. The shaving device according to claim 15, wherein the optical cutting source is a cutting laser.

17. A method for detecting a birefringent object near a surface, comprising the act of:
   emitting first optical radiation over an optical path to the birefringent object, the first optical radiation comprising at least a first wavelength, a second wavelength and an incident polarization state;
   detecting second optical radiation having orthogonal first and second polarization states, the first polarization state corresponding to the incident polarization state, the second optical radiation is the first optical radiation scattered and/or reflected from the birefringent object and the skin surface received over the optical path; and
   distinguishing by a processor between the birefringent object and the surface using the first and second polarization states of the second optical radiation.

* * * * *